US012583921B2

(12) United States Patent (10) Patent No.: US 12,583,921 B2
Saxena (45) Date of Patent: Mar. 24, 2026

(54) TARGETED ANTI-SGLT1 AVIAN IgY ANTIBODIES AS TREATMENT OF PRE-DIABETES, TYPE 2 DIABETES AND GESTATIONAL DIABETES

(71) Applicant: Lay Sciences, Inc., Jupiter, FL (US)

(72) Inventor: Uday Saxena, Hyderabad (IN)

(73) Assignee: Lay Sciences, Inc., Jupiter, FL (US)

( * ) Notice: Subject to any disclaimer, the term of this patent is extended or adjusted under 35 U.S.C. 154(b) by 0 days.

(21) Appl. No.: 18/859,969

(22) PCT Filed: Apr. 26, 2023

(86) PCT No.: PCT/US2023/066248
§ 371 (c)(1),
(2) Date: Oct. 24, 2024

(87) PCT Pub. No.: WO2023/212604
PCT Pub. Date: Nov. 2, 2023

(65) Prior Publication Data
US 2025/0297000 A1 Sep. 25, 2025

(30) Foreign Application Priority Data
Apr. 27, 2022 (IN) ............................. 202241024625

(51) Int. Cl.
*C07K 16/28* (2006.01)
*A61K 39/00* (2006.01)
*A61P 3/10* (2006.01)
(52) U.S. Cl.
CPC ................ *C07K 16/28* (2013.01); *A61P 3/10* (2018.01); *A61K 2039/505* (2013.01); *A61K 2039/542* (2013.01); *C07K 2317/23* (2013.01); *C07K 2317/34* (2013.01); *C07K 2317/76* (2013.01)
(58) Field of Classification Search
None
See application file for complete search history.

(56) References Cited

FOREIGN PATENT DOCUMENTS

KR 20030063972 7/2003

OTHER PUBLICATIONS

Sano Ryuhei et al., "Sodium-glucose cotransporters: Functional properties and pharmaceutical potential," Journal of Diabetes Investigation, vol. 11, No. 4, Apr. 16, 2020, pp. 770-782, XP093060931, Australia.
Song Panai et al., "Sodium glucose contransporter SGLT1 as a therapeutic target in diabetes mellitus," Expert Opinion on Therapeutic Targets, vol. 20, No. 9, Sep. 1, 2016, pp. 1109-1125, XP055878270.
Diez-Sampedro Ana et al., "Sugar Binding Residue Affects Apparent Na+ Affinity and Transport Stoichiometry in Mouse Sodium/Glucose Contransporter Type 3B," Journal of Biological Chemistry, vol. 286, No. 10, Mar. 1, 2011, pp. 7975-7982, XP093060949.
Saxena Uday et al., "Targeted neutralizing IgY antibodies against SGLT1 glucose transporter reduce glucose uptake and improve glycemic profile in vivo," bioRxiv, May 8, 2023, pp. 1-21, XP093060928.

*Primary Examiner* — Ruixiang Li
(74) *Attorney, Agent, or Firm* — Dentons US LLP; Derek A Auito

(57) ABSTRACT

Provided are methods for treating a disorder characterized by elevated blood glucose levels in a subject in need thereof, comprising administering to the subject a therapeutically effective amount of a hyperimmunized egg product obtained from an egg-producing animal, wherein the hyperimmunized egg product comprises a therapeutically effective amount of one or more IgY antibodies to an extracellular glucose binding domain of a sodium-glucose co-transporter SGLT. Also provided are hyperimmunized eggs and egg products produced by an animal that has been hyperimmunized with an antigen that contains an extracellular glucose binding domain of a sodium-glucose co-transporter SGLT or fraction thereof, and use of the hyperimmunized eggs or hyperimmunized egg products to reduce blood glucose levels in a subject, such as to treat type 2 diabetes. Methods or preparing the hyperimmunized eggs and hyperimmunized egg products are also provided.

9 Claims, 3 Drawing Sheets

Specification includes a Sequence Listing.

TARGETED ANTI-SGLT1 AVIAN IgY ANTIBODIES AS TREATMENT OF PRE-DIABETES, TYPE 2 DIABETES AND GESTATIONAL DIABETES

RELATED APPLICATION

This application is the National Stage filing under 35 U.S.C. 371 of International Application No. PCT/US2023/066248, filed Apr. 26, 2023, which claims the benefit of IN application No. 202241024625 filed Apr. 27, 2022, the contents of which are all hereby incorporated by reference herein in their entirety.

FIELD OF INVENTION

The present invention is related to a composition that includes an antibody against a conserved sequence of an extracellular glucose binding domain of a sodium-glucose co-transporter SGLT for inhibiting glucose absorption in a subject, such as for providing a therapy for pre-diabetes, type 2 diabetes and gestational diabetes.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Apr. 25, 2023, is 10 kilobytes in size, and is titled 15809533-6WO_SEQ.xml.

BACKGROUND

Pre-diabetes and Type 2 diabetes prevalence is increasing worldwide. Pre-diabetes is the period of above normal blood glucose levels prior to the onset of full-fledged Type 2 diabetes. It lasts for a few years and is reversible. Gestational diabetes is often seen during second trimester of pregnancy and has to be managed very carefully since drugs are not an option in this situation. While changes in diet or amount of daily exercise can be helpful in the treatment of diabetes, patient compliance can be low, and medication is often prescribed to lower glucose blood levels.

Conventional medications prescribed for diabetes include insulin, insulin analogs, sulfonylureas, and metformin. Some of these drug interventions can be accompanied by adverse side effects such as hypoglycemia, lactic acidosis, or gastrointestinal side effects. While these conventional medications can be effective, many of the medications may be ineffective in subjects that have developed an intolerance to the drug rendering the drug treatment ineffective, or for which contraindications, such as adverse side effects, render the medications inappropriate. Accordingly, a need exists for new acceptable, safe, and effective treatments for the lowering of blood glucose levels as an anti-diabetic treatment for pre-diabetic diabetic patients and gestational diabetes.

BRIEF SUMMARY

Accordingly, provided herein are new compositions and methods for lowering blood glucose levels in a subject.

Sodium-glucose co-transporters SGLT, members of the solute carrier family SLC5, are high-affinity Na+/glucose co-transporters. SGLT1 transports glucose and galactose across the luminal (gut) side of enterocytes and is the first step in the absorption of sugars from diet. In the kidney, SGLT1 is located on the apical (urine) side of the proximal tubule and facilitates the reabsorption of urinary glucose from the glomerular filtrate along with SGLT2 which is predominant family member in the kidney. SGLT1/SGLT2 have a key role in the absorption of glucose in the kidney and/or GI tract.

SGLT1 is the major intestinal transport protein for uptake of dietary glucose. The instant applicants have determined that by antagonizing the binding of dietary glucose to this transport protein, blood glucose lowering will follow. Provided are specific inhibitory antibodies, and in particular avian antibodies (IgY) against the extracellular glucose binding domain of SGLT, such as SGLT1, SGLT2, and SGLT3, and SGLT1 in particular, and methods of using these antibodies to lower blood glucose levels in a subject, such as for a therapy for pre-diabetes, type 2 diabetes, and gestational diabetes.

DETAILED DESCRIPTION

Definitions

Figures 1, 2:
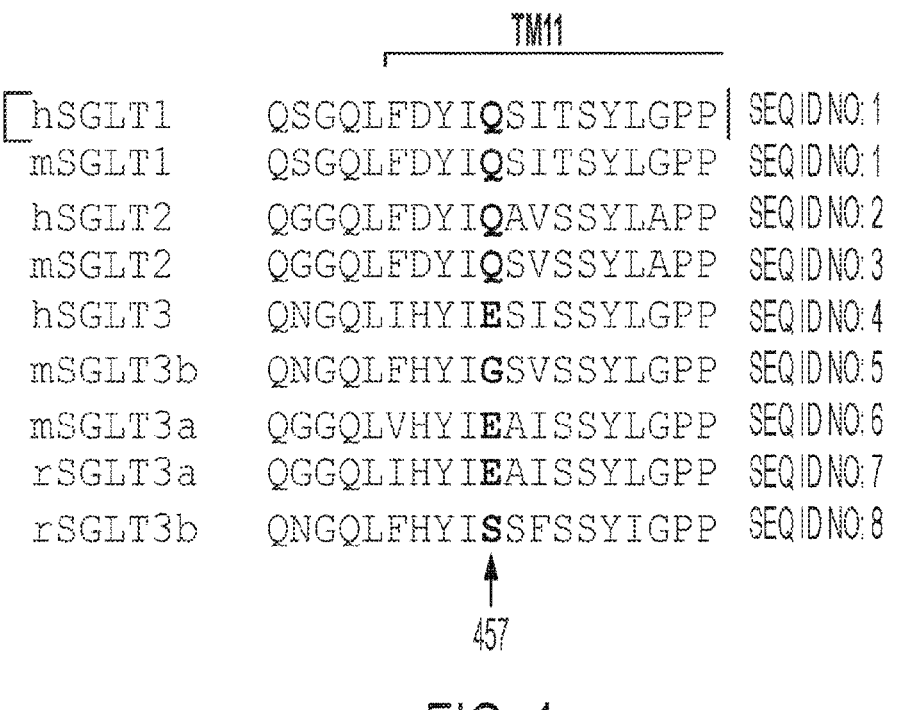
FIG. 1 shows the glucose binding domain of sodium-glucose co-transporters SGLT of several different species.
FIG. 2 is a graph showing binding of IgY to SGLT peptide antigen.

Unless defined otherwise, all technical and scientific terms used herein have the same meaning as is commonly understood by one of skill in the art to which the inventions belong. All patents, patent applications, published applications and publications, websites and other published materials referred to throughout the entire disclosure herein, unless noted otherwise, are incorporated by reference in their entirety.

In the event that there is a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein, the singular forms "a," "an" and "the" include plural referents unless the context clearly dictates otherwise.

As used herein, all ranges include the upper and lower limits. As used herein, the recitation of a numerical range for a variable is intended to convey that the variable can be equal to any value(s) within that range, as well as any and all sub-ranges encompassed by the broader range. Thus, the variable can be equal to any integer value or values within the numerical range, including the end-points of the range.

As an example, a variable which is described as having values between 0 and 10, can be 0, 4, 2-6, 2.75, 3.3-4.4, etc.

As used herein, "about" is a term of approximation and is intended to include minor variations in the literally stated amounts, as would be understood by those skilled in the art. Such variations include, for example, standard deviations associated with techniques commonly used to measure the amounts of the constituent elements or components of an alloy or composite material, or other properties and characteristics. All of the values characterized by the above-described modifier "about," are also intended to include the exact numerical values associated therewith. Hence "about 5 percent" means "about 5 percent" and also "5 percent."

As used herein, "optional" or "optionally" means that the subsequently described event or circumstance does or does not occur, and that the description includes instances where said event or circumstance occurs and instances where it does not. For example, an optional component in a composition means that the component may be present or may not be present in the composition.

As used herein, the terms "comprises" and "comprising" are inclusive and open ended, and not exclusive. When used in the specification and claims, the terms "comprises" and "comprising" and variations thereof mean the specified features, steps or components are included, but do not exclude other features, steps or components.

Any compositions described herein are intended to encompass compositions which consist of, consist essentially of, as well as comprise, the various constituents identified herein, unless explicitly indicated to the contrary.

In the specification and claims, the singular forms include plural referents unless the context clearly dictates otherwise. As used herein, unless specifically indicated otherwise, the word "or" is used in the "inclusive" sense of "and/or" and not the "exclusive" sense of "either/or."

As used herein, the term "exemplary" means "serving as an example or illustration," and should not be construed as being preferred or advantageous over other configurations disclosed herein.

Unless indicated otherwise, each of the individual features or embodiments of the present specification are combinable with any other individual feature or embodiment that are described herein, without limitation. Such combinations are specifically contemplated as being within the scope of the present invention, regardless of whether they are explicitly described as a combination herein.

As used herein, the term "subject" includes members of the animal kingdom including but not limited to human beings.

The term "hyperimmunization" means repeated exposure to one or more antigens such that an immune response is elevated and maintained above the natural unexposed state.

A "hyperimmune state" refers to an elevated immune response in an egg producing animal that has been hyper-immunized.

The term "egg" as used herein refers to a whole egg (table, hyperimmunized or otherwise). The term "egg product" as used herein refers to a whole egg or any product or fraction obtained from a whole egg. In a particular embodiment, the egg product is an egg yolk, for example, an egg yolk powder. In another embodiment, the egg product is an egg white, for example, an egg white powder. In another embodiment, the egg product is obtained from a whole egg, for example, a whole egg powder (e.g., a spray-dried whole egg powder).

The term "control egg" refers to an egg obtained from an egg-producing animal that is not maintained in a hyperim-munized state, i.e., an animal that has not been hyperimmunized. The term "control egg product" refers to a control egg or an egg product obtained from a control egg.

The term "hyperimmunized egg" refers to a whole egg obtained from an egg-producing animal maintained in a hyperimmune state, i.e., an egg-producing animal that has been hyperimmunized. The term "hyperimmunized egg product" refers to a hyperimmunized egg or any product obtained from a hyperimmunized egg.

In certain embodiments, the hyperimmunized egg product is a concentrate. As used herein the term "concentrate" refers to a hyperimmunized egg product that is at least partially purified, such that the concentration of antibodies in the concentrate is greater than the concentration of antibodies in a hyperimmunized egg.

The term "egg powder" refers to a whole egg that has been dried. In some embodiments, the egg powder is spray-dried.

The term "egg-producing animal" means any oviparous animal, and includes any animal that lays an egg, such as avians, fish and reptiles.

The term "avian" refers to an animal that is a member of the class Aves. Avians include, but are not limited to, chickens, turkeys, geese, ducks, pheasants, quail, pigeons and ostriches.

The term "supranormal levels" means levels in excess of those found in eggs of egg-producing animals that are not hyperimmunized. For example, supranormal levels of an antibody to a particular antigen are levels of the antibody in excess of those found in eggs of egg-producing animals that are not hyperimmunized with the particular antigen.

The term "administer" means any method of providing a subject with a substance, such as orally.

The term "antigen" refers to a substance that is able to induce a humoral antibody and/or cell-mediated immune response rather than immunological tolerance. The term signifies the ability to stimulate an immune response as well as react with the products of it, e.g., an antibody.

As used herein, an "antibody" is a protein that includes at least one complementarity determining region that binds to a specific target antigen. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. In a particular embodiment, the antibody is a polyclonal antibody. The term "polyclonal antibody", as used herein, refers to a population of antibody molecules that that are capable of immunoreacting with different epitopes on a particular antigen. In a particular embodiment, the antibody is an IgY antibody.

As used herein, the term "effective amount" refers to the amount of hyperimmunized egg product which when administered to a subject is sufficient to prevent or treat a disease characterized by high blood glucose levels. The effective amount can vary depending, for example, on the age, weight, and/or health of the subject to be treated.

Anti-SGLT Antibodies

Up to 70% of the blood glucose is derived thru the diet, therefore inhibition of intestinal SGLT1 function is an exciting new approach to glucose lowering anti-diabetic concept. SGLT is strongly expressed in the apical brush border of the small intestine and the late proximal tubule of the kidney, where it is critical for absorption/reabsorption of glucose into the blood stream, while SGLT1 acts primarily in the gut to absorb glucose molecules from dietary glucose, SGLT2 acts primarily in the kidney to reabsorb glucose filtered by the renal glomerulus (Sano et al., J Diabetes Investigat 11: 770-782 (2020). The interaction of anti-SGLT antibodies with SGLT, such as SGLT1, results in SGLT1 inhibition of glucose absorption, and will lower blood glucose in diabetic patients by reducing dietary glucose absorption in the intestine as well as by increasing the release of gastrointestinal incretins like glucagon-like peptide-1. In short-term studies, inhibition of SGLT1 and combined SGLT1/SGLT2 inhibition appeared to be safe and not associated with increased rates of hypoglycemia or clinically relevant gastrointestinal side effects. hSGLT3 has been shown to act as a sugar sensor in vivo, and that mutating the glutamate at position 457 in hSGLT3 to glutamine, the amino acid present in all SGLT1 proteins results in hSGLT3 exhibiting sugar transporter functionality similar to SGLT1 (Bianchi et al., (2010), PLOS ONE 5(4): e10241, doi: 10.1371/journal.pone.0010241, 11 pages).

As mentioned above, SGLT1 is mainly expressed on the apical membrane (i.e., the gut side) of enterocytes. It is also present in the kidney (in the latter part of renal proximal tubule), the heart, and the parotid and submandibular salivary glands. SGLT1 is a 75-kDa membrane protein with 14 transmembrane α-helices, an extracellular amino terminus and an intracellular carboxyl terminus. SGLT1 is responsible for the sodium-dependent, active uptake of glucose across the apical membrane of the small intestine. In the kidney, SGLT1 is responsible for about 10% of the tubular glucose reabsorption. SGLT1 has a high affinity but a low capacity for transporting glucose. The preferred substrates of SGLT1 are D-glucose and D-galactose, whereas mannose is only slightly transported.

The extracellular glucose binding domain in the SGLT family has been identified and its functional role in glucose transport in the gut and kidney has been delineated (see Wright et al., Physiol Rev 91:733-794 (2011); and Liu, Tiemin. "Structure/Function Studies of the High Affinity Na+/Glucose Cotransporter (SGLT1)." PhD dissertation, University of Toronto, 2006). A portion of one of the 14 transmembrane helices (TM11), which is part of extracellular loop EL6 (Han et al., Nature 601 (7892): 274-279 (2022)), having the sequence QSGQLFDYIQSITSYLGPP (SEQ ID NO:1), was selected because of its sequence conservation across species, as show in Table A below.

TABLE A

| Species | Sequence |
| --- | --- |
| Cat | QSGQLFDYIQSITSYLGPP |
| Dog | QSGQLFDYIQSITSYLGPP |
| Sheep | QSGQLFDYIQSITSYLGPP |
| Mouse | QSGQLFDYIQSITSYLGPP |
| Horse | QSGQLFDYIQSITSYLGPP |
| Human | QSGQLFDYIQSITSYLGPP |
| Rabbit | QSGQLFDYIQSITSYLGPP |

This portion of glucose binding domain can be exploited to antagonize the binding of glucose to SGLT1 by administering antibodies to the glucose binding domain and thus prevent dietary glucose absorption.

The present invention provides a formulation of IgY polyclonal antibodies against a conserved sequence of an extracellular glucose binding domain in a sodium-glucose co-transporter SGLT for inhibiting glucose absorption in a subject, such as for providing an oral therapy for type 2 diabetes. The formulation is designed to interfere with uptake of dietary glucose, as the antibodies bind to the major intestinal transport protein for uptake of dietary glucose, thereby lowering blood glucose levels. The antibodies bind to this part of the extracellular domain as antagonists. In some embodiments, the anti-SGLT antibodies are IgY antibodies prepared in an avian system.

In one embodiment, the formulation can contain a whole hyperimmune egg, a hyperimmune egg yolk, or a spray dried whole hyperimmune egg, or spray dried hyperimmune egg yolk that contains the anti-SGLT1 IgY antibodies. In one embodiment, the formulation contains partially purified or purified anti-SGLT1 IgY antibodies.

Utilizing blast searches, the instant applicants have identified a 19 amino acid sequence that appears to be the most conserved amino acid stretch in the extracellular glucose binding domain amongst human and animal species suggesting it is critical in glucose uptake (see FIG. 1). Using an antigen that contains at least these 19 amino acid peptides, a vaccine can be prepared to immunize an avian species, such as chickens, and the resulting IgY antibodies directed to the extracellular glucose binding domain can be harvested from the eggs of the immunized chickens. In some embodiments, the antigen in the vaccine used to immunize chickens includes the domain of 19 amino acids of human SGLT1, which is the major protein in the intestine for glucose absorption. Hyperimmune whole egg or fractions thereof, such as egg yolk, could be used as an over-the-counter treatment to lower glucose uptake and thereby blood glucose in a subject to which the hyperimmune whole egg or fractions thereof are administered. IgY antibodies can be raised to any one or more of the extracellular glucose binding domains of SGLT shown in FIG. 1, alone or in combination, and the resulting IgY antibodies can be used as an orally administered composition for the treatment of a disease or condition characterized by increased blood glucose levels, such as diabetes or prediabetes, and in particular as an oral therapy for type 2 diabetes.

The IgY antibody to the extracellular glucose binding domain of SGLT also can be purified as a new biological entity (NBE) for administration to subjects in need of lowering blood glucose levels.

Also provided are methods preparing polyclonal IgY antibodies directed to an antibody that binds to a conserved sequence of an extracellular glucose binding domain in a sodium-glucose co-transporter SGLT protein. The extracellular glucose binding domain can include a sequence selected from among: QSGQLFDYIQSITSYLGPP (SEQ ID No.:1), QGGQLFDYIQAVSSYLAPP (SEQ ID NO:2), QGGQLFDYIQSVSSYLAPP (SEQ ID NO:3), QNGQLIHYIESISSYLGPP (SEQ ID NO:4), QNGQLFHYIGSVSSYLGPP (SEQ ID NO:5), QGGQLVHYIEAISSYLGPP (SEQ ID NO:6), QGGQLIHYIEAISSYLGPP (SEQ ID NO: 7) and QNGQLFHYISSFSSYIGPP (SEQ ID NO:8). The polyclonal IgY antibodies can be harvested from chicken eggs hyperimmunized with the conserved sequence of an extracellular glucose binding domain in a sodium-glucose co-transporter SGLT protein, and the yolks pooled.

The vaccine used for inoculating the chickens can include the conserved sequence of an extracellular glucose binding domain in a sodium-glucose co-transporter SGLT protein and an adjuvant (Freund's—complete or incomplete, MPL, etc.) or with TLR agonists or with cytokines to improve immune responses in chickens. The harvested antibodies from hyperimmunized chickens can be used as a prophylactic or therapeutic formulation directly as IgY-containing egg yolk, IgY-containing whole egg powder, or can include purified or partially purified IgY antibodies extracted from the hyperimmunized eggs for use for oral administration or as purified IgY polyclonal protein therapeutically when administered orally.

Uses

The anti-SGLT IgY antibodies of the invention are useful for the treatment of disease conditions in subjects, mammals in particular, including humans, and in particular disease conditions characterized by high glucose blood levels. The subject can have elevated blood glucose levels, alone or in combination with elevated hemoglobin A1C levels. The subject can be pre-diabetic or diabetic. The anti-SGLT IgY antibodies of the invention can be used as a therapeutic for the treatment of type 2 diabetes.

Hyperimmunized Egg Product

Also provided is a method of preparing a hyperimmunized egg product, the method comprising: a) hyperimmunizing an egg-producing animal with a composition comprising an antigen that includes a conserved sequence of an extracellular glucose binding domain in a sodium-glucose co-transporter SGLT protein; and b) preparing a hyperimmunized egg product from one or more eggs produced by the animal. In some embodiments, the antigen comprises or consists of a conserved region of an extracellular glucose binding domain having a sequence selected from among:

```
                                      (SEQ ID NO: 1)
QSGQLFDYIQSITSYLGPP, (SEQ ID NO: 2)
QGGQLFDYIQAVSSYLAPP, (SEQ ID NO: 3)
QGGQLFDYIQSVSSYLAPP, (SEQ ID NO: 4)
QNGQLIHYIESISSYLGPP, (SEQ ID NO: 5)
QNGQLFHYIGSVSSYLGPP, (SEQ ID NO: 6)
QGGQLVHYIEAISSYLGPP, (SEQ ID NO: 7)
QGGQLIHYIEAISSYLGPP,
and (SEQ ID NO: 8)
QNGQLFHYISSFSSYIGPP.
```

Egg-producing animals produce antibodies in blood and eggs that are specific to particular immunogens. For example, various genera of the class Aves, such as chickens (Gallus domesticus), turkeys, and ducks produce antibodies against antigens associated with avian diseases. LeBacq-Verheyden et al. (Immunology 27:683 (1974)) and Leslie, G.A., et al. (J. Med. 130:1337 (1969)), have quantitatively analyzed immunoglobulins of the chicken. Polson, A., et al. (Immunological Communications 9:495-514 (1980)) immunized hens against several proteins and natural mixtures of proteins, and detected IgY antibodies in the yolks of the eggs. Fertel, R., et al. (Biochemical and Biophysical Research Communications 102:1028-1033 (1981)) immunized hens against prostaglandins and detected antibodies in the egg yolk. Jensenius et al. (Journal of Immunological Methods 46:63-68 (1981)) provide a method of isolating egg yolk IgG for use in immunodiagnostics. Polson et al. (Immunological Communications 9:475-493 (1980)) describe antibodies isolated from the yolk of hens that were immunized with a variety of plant viruses.

U.S. Pat. No. 4,748,018 discloses a method of passive immunization of a mammal that comprises parenterally administering purified antibody obtained from the eggs of an avian that has been immunized against the corresponding antigen, and wherein the mammal has acquired immunity to the eggs. U.S. Pat. No. 5,772,999, assigned to DCV-Biologics, discloses a method of preventing, countering or reducing chronic gastrointestinal disorders or Non-Steroidal Anti-Inflammatory Drug-induced (NSAID-induced) gastrointestinal damage in a subject by administering hyperimmunized egg and/or milk or fractions thereof to the subject.

An immunized egg is an egg which comes from an avian which has been immunized with, for example, a specific antigen or mixture of antigens. A hyperimmunized egg is an egg which comes from an avian which has been brought to a specific state of immunization by means of, for example, periodic booster administrations of antigens. Hyperimmunized eggs, no matter the type of antigen their avian maker has been administered, have been found to have various beneficial factors, including, as mentioned above, the treatment of chronic gastrointestinal disorders, NSAID-induced gastrointestinal damage (see U.S. Pat. No. 5,772,999) and anti-inflammatory effects due to the presence of an anti-inflammatory composition (see U.S. Application Publication No. US 2004/0156857).

One of the advantages of the hyperimmunized egg product is that it would have a higher and more consistent level of antibodies (e.g., IgY antibodies) to one or more of the antigens described herein compared to a control egg product or an egg product from a chicken that has been immunized with the antigen using standard immunization techniques. Typically standard immunization consists of an initial immunization followed by one or two booster immunization at 30 day intervals. In some embodiments, hyperimmunization comprises at least 4, 5, 6, 7, 8, 9 or 10 immunizations with an antigen described herein. In some embodiments, hyperimmunization comprises immunizing an egg producing animal with an antigen described herein at intervals of less than 30 days, less than 25 days, less than 20 days, less than 15 days, less than 10 days, or less than 5 days. In some embodiments, hyperimmunization comprises immunizing an egg producing animal with an antigen described herein at an interval of 1 week, 2 weeks, 3 weeks, 4 weeks, 1 month, 2 months or 3 months. Any of these values may be used to define a range for the interval at which the egg producing animal is immunized. For example, in some embodiments, the egg producing animal is hyperimmunized at an interval ranging from once every 2 weeks to once every 3 months, once per week to once every 3 months, or once every 2 weeks to once per month.

The hyperimmunized egg product can be produced by any egg-producing animal. It is preferred that the animal be a member of the class Aves or, in other words, an avian. Within the class Aves, domesticated fowl are preferred, but other members of this class, such as turkeys, ducks, and geese, are a suitable source of hyperimmune egg product. In a particular embodiment, the egg-producing animal is a chicken.

The hyperimmunization state can be achieved by administering an initial immunization, followed by periodic boosters with sufficiently high doses of specific antigens or mixtures of antigens. The dosage of the booster may be 10%, 20%, 30%, 40%, 50%, 60%, 70%, 80%, 90% or 100% of the dosage necessary to produce primary immunization of the egg-producing animal. Any of these percentages may be used to define a range for the dosage of the booster immunization. For example, in some embodiments, the dosage of the booster is 20%-80%, 30%-70%, or 50%-100% of the dosage necessary to produce primary immunization of the egg-producing animal. In a particular embodiment, the dosage of the booster immunization is 50% of the dosage of the primary immunization.

Having knowledge of the requirement for developing and maintaining a hyperimmune state, it is within the skill of the art to vary the amount of antigen administered, depending on the egg-producing animal genera and strain employed, in order to maintain the animal in the hyperimmune state.

The hyperimmune state may be produced by a single antigen or a combination of antigens. Hyperimmunization may be achieved by multiple exposures to multiple antigens, or multiple exposures to a single antigen.

Antigens for Hyperimmunization

In some embodiments, an antigen for hyperimmunization can comprise a protein that includes a sequence of a sodium-glucose co-transporter (SGLT). The antigen for hyperimmunization can comprise one or more immunogenic fragments of an extracellular glucose binding domain in a sodium-glucose co-transporter (SGLT). The antigen for hyperimmunization can comprise one or more immunogenic fragments of an extracellular glucose binding domain of SGLT1, SGLT2, SGLT3, or any combination thereof. The antigen for hyperimmunization can comprise a combination of SGLT1protein and SGLT2 protein, or a fusion protein that contains both SGLT1 and SGLT2 sequences. The antigen for hyperimmunization can comprise a combination one or more extracellular glucose binding domain of an SGLT1 protein and one or more extracellular glucose binding domains of an SGL2 protein. The antigen for hyperimmunization can comprise a fusion protein that contains one or more extracellular glucose binding domains of an SGLT1 protein and one or more extracellular glucose binding domains of an SGLT2 protein.

In some embodiments, the antigens for hyperimmunization comprise one or more immunogenic fragments of an extracellular glucose binding domain in a sodium-glucose co-transporter SGLT. In some embodiments, an immunogenic fragment as described herein can include at least 10, 20, 30, 40, 50, 60, 70, 80, 90, or 100 amino acid residues. The antigens for hyperimmunization can comprise one or more immunogenic fragments of an extracellular glucose binding domain in a sodium-glucose co-transporter SGLT where the fragment(s) include a sequence selected from among:

```
                                          (SEQ ID NO: 1)
QSGQLFDYIQSITSYLGPP, (SEQ ID NO: 2)
QGGQLFDYIQAVSSYLAPP, (SEQ ID NO: 3)
QGGQLFDYIQSVSSYLAPP,
```

-continued

```
                                          (SEQ ID NO: 4)
QNGQLIHYIESISSYLGPP, (SEQ ID NO: 5)
QNGQLFHYIGSVSSYLGPP, (SEQ ID NO: 6)
QGGQLVHYIEAISSYLGPP, (SEQ ID NO: 7)
QGGQLIHYIEAISSYLGPP,
and (SEQ ID NO: 8)
QNGQLFHYISSFSSYIGPP.
```

The antigens for hyperimmunization can comprise or be a fragment containing 20 to 40 amino acid residues containing a sequence selected from among:

```
                                          (SEQ ID NO: 1)
QSGQLFDYIQSITSYLGPP, (SEQ ID NO: 2)
QGGQLFDYIQAVSSYLAPP, (SEQ ID NO: 3)
QGGQLFDYIQSVSSYLAPP, (SEQ ID NO: 4)
QNGQLIHYIESISSYLGPP, (SEQ ID NO: 5)
QNGQLFHYIGSVSSYLGPP, (SEQ ID NO: 6)
QGGQLVHYIEAISSYLGPP,
and (SEQ ID NO: 7)
QNGQLFHYISSFSSYIGPP.

The antigens for hyperimmunization can be
one or a combination of
                                          (SEQ ID NO: 1)
QSGQLFDYIQSITSYLGPP, (SEQ ID NO: 2)
QGGQLFDYIQAVSSYLAPP, (SEQ ID NO: 3)
QGGQLFDYIQSVSSYLAPP, (SEQ ID NO: 4)
QNGQLIHYIESISSYLGPP, (SEQ ID NO: 5)
QNGQLFHYIGSVSSYLGPP, (SEQ ID NO: 6)
QGGQLVHYIEAISSYLGPP, (SEQ ID NO: 7)
QGGQLIHYIEAISSYLGPP,
and (SEQ ID NO: 8)
QNGQLFHYISSFSSYIGPP.

The antigen for hyperimmunization can be
                                          (SEQ ID NO: 1)
QSGQLFDYIQSITSYLGPP, alone or in combination with one or more
selected from among
                                          (SEQ ID NO: 2)
QGGQLFDYIQAVSSYLAPP,
```

-continued (SEQ ID NO: 3)
QGGQLEDYIQSVSSYLAPP (SEQ ID NO: 4)
QNGQLIHYIESISSYLGPP, (SEQ ID NO: 5)
QNGQLFHYIGSVSSYLGPP, (SEQ ID NO: 6)
QGGQLVHYIEAISSYLGPP, (SEQ ID NO: 7)
QGGQLIHYIEAISSYLGPP,
and (SEQ ID NO: 8)
QNGQLFHYISSFSSYIGPP.

Hyperimmunization Procedure

The following list of steps is an example of a procedure that can be used to bring an egg-producing animal to a heightened state of immunity from which the resultant hyperimmune egg or egg product can be harvested.

1. Selecting one or more antigens.
2. Eliciting an immune response in the egg-producing animal by primary immunization.
3. Administering booster vaccines of one or more antigens of appropriate dosage to induce and maintain the hyperimmune state.

Step 1: The selected antigen(s) must be capable of inducing immune and hyperimmune states in the egg-producing animal. In some embodiments, the egg-producing animal is immunized with an antigen selected from:

(a) one or more than one immunogenic fragment of an extracellular glucose binding domain of a sodium-glucose co-transporter SGLT, where the immunogenic fragment can include at least 10, 20, 30, 40, 50, 60, 70, 80, 90, or 100 amino acid residues; or (b) one or more than one immunogenic fragment of an extracellular glucose binding domain of a sodium-glucose co-transporter SGLT where the fragment(s) include(s) a sequence selected from among: QSGQLFDYIQSITSYLGPP (SEQ ID NO:1), QGGQLFDYIQAVSSYLAPP (SEQ ID NO:2), QGGQLFDYIQSVSSYLAPP (SEQ ID NO:3), QNGQLIHYIESISSYLGPP (SEQ ID NO:4), QNGQLFHYIGSVSSYLGPP (SEQ ID NO:5), QGGQLVHYIEAISSYLGPP (SEQ ID NO:6), QGGQ-LIHYIEAISSYLGPP (SEQ ID NO:7), and QNGQLFHYISSFSSYIGPP (SEQ ID NO:8).

Step 2: The antigen is used to be prepare a vaccine and can be administered by any method that elicits an immune response. It is preferred that immunization be accomplished by administering the vaccine through intramuscular or subcutaneous injection. The preferred muscle for injection in an avian is the breast muscle. Dosage is preferably 0.05-5 milligrams of the immunogenic vaccine. Other methods of administration that can be used include intravenous injection, intraperitoneal injection, intradermal, rectal suppository, aerosol or oral administration.

It can be determined whether the vaccine has elicited an immune response in the egg-producing animal through a number of methods known to those having skill in the art of immunology. Examples of these include enzyme-linked immunosorbent assays (ELISA), tests for the presence of antibodies to the stimulating antigens, and tests designed to evaluate the ability of immune cells from the host to respond to the antigen. The minimum dosage of antigen necessary to induce an immune response depends on the vaccination procedure used, including the type of adjuvants and formulation of antigen(s) used as well as the type of egg-producing animal used as the host.

Step 3: The hyperimmune state can be induced and maintained in the target animal by repeated booster administrations of an appropriate dosage of vaccine at fixed time intervals. The time intervals can be one week to three-month intervals over a period of 6-12 months. However, the booster administrations are administered so that they do not lead to immune tolerance. Methods of preparing the hyperimmunized egg product are described, for example, in U.S. Pat. No. 6,803,035 Greenblatt et al., 2004), which is incorporated by reference herein in its entirety.

In a particular embodiment, an antigen as described herein is formulated into a vaccine containing an adjuvant. The adjuvant can selected from among Freund's complete adjuvant, Freund's incomplete adjuvant, a saponin, a biodegradable polymer, aluminum hydroxide, mineral oil, a surfactant, and combinations thereof. Exemplary saponins include QS-21 and Quil A. Exemplary biodegradable polymers include chitosan, zymosan, a poly(ethylene glycol)-block-poly(propylene glycol)-block-poly(ethylene glycol), such as Pluronic® L121 block copolymer, poly(lactic acid), poly (glycolic acid), poly(lactic-co-glycolic acid), polycaprolactone, and combinations thereof. Exemplary surfactants include polysorbate 80 and sorbitan trioleate.

In any exemplary vaccination schedule, in the first vaccination, the egg-producing animal can be given two 0.5 ml doses of the vaccine. One to two weeks later, one 0.5 ml dose of vaccine can be administered to the egg-producing animal as a booster vaccination. An additional booster vaccination can be performed 3 to 6 weeks after the first vaccination. The vaccines can be administered intramuscularly, such as to breast tissue.

It is possible to use other hyperimmunization maintenance procedures or combination of procedures, such as, for example, intramuscular injection for primary immunization and intravenous injection for booster injections. Further procedures include simultaneously administering microencapsulated and liquid antigen, or intramuscular injection for primary immunization, and booster dosages by oral administration or parenteral administration by microencapsulation means. Several combinations of primary and hyperimmunization are known to those skilled in the art.

The antibody can be an IgA, IgM or IgY antibody. In a particular embodiment, the antibody is an IgY antibody. The IgY antibody can be polyclonal antibodies, each of which can react with different epitopes of the same antigen. For example, the IgY antibody produced by the methods described herein can react with one or several epitopes of extracellular glucose binding domain of a sodium-glucose co-transporter SGLT, or can react with one or several epitopes of extracellular glucose binding domain of a sodium-glucose co-transporter SGLT1.

Comparisons of antibody titers in hyperimmunized egg products and control egg products can be determined by methods known in the art. For example, in one embodiment, eggs are collected and the antibody titers are monitored by ELISA at regular intervals. To determine antibody titers, total IgY is extracted from eggs using Pierce™ Chicken IgY Purification Kit (Thermo Fisher Scientific, Waltham, MA). Briefly, 2 mL of egg is mixed with five volumes of delipidation reagent and IgY is purified following the manufacturer's instructions. Spray dried egg powder samples are reconstituted in sterile PBS at 1 mg/mL, and filtered through a 0.22 μm membrane filter. Specific antibody titers in the isolated IgY or egg powder samples are measured by ELISA. Flat bottom, 96-well microtiter plates (Corning® Costar®, Corning, NY) are coated with purified recombinant proteins (e.g., Antigens B, C, Col, or Co2) at 10 μg/mL (100 μL/well) and incubated overnight at 4° C. The plates are washed twice with PBS containing 0.05% Tween 20 (Sigma-Aldrich, St. Louis, MO) and blocked with 100 μL/well of PBS containing 1% Bovine Serum Albumin (BSA) and incubated for 1 h at RT. Serially diluted (in PBS with 0.1% BSA) IgY samples from egg powder samples are added to the plates in triplicate wells (100 μL/well) and incubated for 2 h at RT with constant shaking. The plates are then washed with PBS-T and treated with peroxidase-conjugated rabbit anti-chicken IgY (IgG) antibody (1:500; Sigma), incubated for 30 min, followed by color development for 10 minutes with 0.01% tetramethylbenzidine substrate (Sigma) in 0.05 M Phosphate-Citrate buffer, pH 5.0. Bound antibodies are detected by measuring optical density at 450 nm (OD450) using a microplate reader (Bio-Rad, Hercules, CA).

In some embodiments, the hyperimmunized egg or egg product comprises at least 0.0001%, 0.0005%, 0.001%, 0.005%, 0.01%, 0.05%, or 0.1% by weight of an IgY antibody to a specific antigen disclosed herein. Typically, a whole chicken egg weighs approximately 60 grams without the shell, with the egg yolk weighing approximately 20 grams and the egg white weighing approximately 40 grams. In some embodiments, 3 grams of egg yolk contains about 20-30 milligrams of total IgY, such that a whole egg contains about 150-200 mg total IgY. In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 25% or 30% of the total IgY in the hyperimmunized egg or egg product is specific to one of the antigens used for hyperimmunization.

Antibody titers may be expressed by the highest fold dilution of egg product that still contains detectable antibodies as measured by optical density as described above. For example, an antibody titer of 1000 would indicate that a 1000-fold dilution of the egg product contains detectable antibody, but higher dilutions do not contain detectable antibody. In some embodiments, the antibody titer in the hyperimmunized egg product can be at least 50,000, at least 80,000, at least 100,000, at least 160,000, at least 250,000, at least 320,000 at least 500,000, at least 640,00, or at least 1 million, 2million, 3 million, 4 million, 5 million, 6 million, 7 million, 8 million, 9 million, 10 million, 11 million, 12 million, 13 million, 14 million, 15 million, 16 million, 17million, 18 million, 19 million, or 20 million. In a particular embodiment, the antibody titer in the hyperimmunized egg product is at least 80,000.

Compositions and Administration

In certain aspects, the present disclosure relates to a method for lowering blood glucose levels in a subject in need thereof, comprising administering to the subject a therapeutically effective amount of a hyperimmunized egg product obtained from an egg-producing animal, thereby lowering blood glucose levels in the subject, wherein the hyperimmunized egg product comprises one or more antibodies that react with one or several epitopes of extracellular glucose binding domain of a sodium-glucose co-transporter SGLT, or that react with one or several epitopes of extracellular glucose binding domain of a sodium-glucose co-transporter SGLT1.

Once the egg-producing animals have been sufficiently hyperimmunized, it is preferred that the eggs from these animals are collected and processed to produce a hyperimmunized egg product in administrable form. Before processing the egg yolk or whole egg, any contaminants which may be present, such as Salmonella or yeast, can be destroyed by heat treatment (pasteurization). The preferred sterilization temperature at which the IgY titer is unaffected is 61° C., and the sterilization time can be 1 to 5 minutes, such as 3 to 5 minutes.

The hyperimmunized egg product can be prepared by dehydration, spray drying, or freeze drying of whole egg, yolk or purified IgY fraction. The dried hyperimmunized egg product can be mixed with an agent such as silicon or silicon derivatives that improves flow properties. The dried hyperimmunized egg product can be stored in a vessel that includes a desiccant. The hyperimmunized egg product can be stored at ambient temperature or refrigerated, for example, at 4° C.

In some embodiments the hyperimmunized egg product can be encapsulated. Methods of encapsulating antibodies and other proteins are known in the art and are described, for example, in U.S. Pat. No. 7,105,158. Materials that are biodegradable and nonantigenic can be used as the encapsulating material. Encapsulating materials include, but are not limited to albumin, PLGA, globulin, natural and synthetic polymers, and thermoplastic polymers. Any polymer that is biocompatible and bioerodible can be used for encapsulation.

In some embodiments, the hyperimmunized egg product can be in the form of a microparticle or nanoparticle, for example, an encapsulated microparticle or encapsulated nanoparticle. The microparticles and nanoparticles can have any shape. Typically the microparticles and nanoparticles are spherical. Other suitable shapes include, but are not limited to, flakes, triangles, ovals, rods, polygons, needles, tubes, cubes and cuboid structures. In certain embodiments, the microparticles have a diameter of less than 10, 9, 8, 7, 6, 5, 4, 3, 2, 1, 0.9, 0.8, 0.7, 0.6, 0.5, 0.4, 0.3, 0.2 or 0.1 micron(s). Any of these values may be used to define a range for the diameter of the microparticle. For example the diameter of the microparticle may be from about 0.1 to about 10 microns, from about 0.1 to about 1 micron, or from about 0.1 to about 2 microns. In other embodiments, larger microparticles or particles may be used. For example the microparticles can have a diameter ranging from 10 microns to 1000 microns. In certain embodiments, the nanoparticles can have a diameter of less than 1000, 900, 800, 700, 600, 500, 400, 300, 200, 100, or 10 nm. Any of these values may be used to define a range for the diameter of the nanoparticle. For example, the diameter of the nanoparticle may be from about 10 to about 1000 nm, from about 100 to about 1000 nm, or from about 10 to about 100 nm.

There are several processes whereby microparticles or nanoparticles can be encapsulated, including, for example, multi-walled microencapsulation, hot melt encapsulation, phase separation encapsulation, spontaneous emulsion, solvent evaporation microencapsulation, solvent removal microencapsulation, and coacervation. These methods are known in the art. Detailed descriptions of the methods are discussed in Mathiowitz et al., "Microencapsulation", in Encyclopedia of Controlled Drug Delivery, vol. 2, pp. 495-546, 1999, John Wiley & Sons, Inc., New York, N.Y., which is incorporated by reference herein in its entirety.

In some embodiments, the IgY antibody specific for an antigen disclosed herein is administered to the subject in a concentrated form. For example, in some embodiments, the IgY antibody is purified or partially purified and concentrated before administration to the subject. Methods of purifying and concentrating IgY antibodies from egg products are known in the art and are described, for example, in U.S. Pat. No. 5,367,054 (Lee, 1994), which is incorporated by reference herein in its entirety.

In some embodiments, the hyperimmunized egg products described herein are used to treat a subject that has elevated blood glucose levels. The subject can be diabetic. The subject can be pre-diabetic. In a particular embodiment, the subject to which the hyperimmunized egg product is administered is a human.

In certain embodiments, the hyperimmunized egg product disclosed herein can be administered to the subject by oral administration. Egg and egg yolk are natural food ingredients and are non-toxic and safe for oral consumption.

The hyperimmunized egg product or anti-SGLT antibody disclosed herein can be included in a food product to be consumed orally. The hyperimmunized egg product or anti-SGLT antibody disclosed herein can be dispersed in a lipid phase of the food product, or dissolved in an aqueous phase of the food product. The food product can be a full calorie or a reduced calorie food product. The food product can contain sugar. The food product can contain no added sugar. The food product can be sugar free. The food product can include a non-nutritive sweetener. The food product can include a high intensity sweetener. The food product can be or comprise a chocolate, such as milk chocolate, bittersweet chocolate, dark chocolate, white chocolate, or flavored chocolate. The food product can be or comprise a confectionery composition, such as, but not limited to, a gelled candy, a chewy candy, a gummy candy, a jelly candy, a lollipop, a candy cane, a tableted candy, a hard candy, a caramel, a fudge, a toffee, a taffy, a licorice, a gum drop, a jelly bean, a nougat, or a fondant, any one of which can include a chocolate coating, a hard shell coating, or compound coating. The food product can be a bar, e.g., a breakfast bar, a candy bar, an energy bar, a protein bar, or a snack bar. The food product can be a filling placed in a baked good, such as a cookie, pastry, or cake, or a frosting placed on a baked good, such as a cookie, pastry, or cake. The food product can be or contain a nut spread, such as almond butter, cashew butter, hazelnut butter or spread, such as NUTELLA® hazelnut spread, or peanut butter. The food product can be a chewing gum. The food product can be a filled confectionary, a lozenge, a pastille, or a mint candy. The food product can be an oral care film or strip, such as a breath freshening film or strip. The food product can be a beverage, such as a fruit drink, a protein drink, a meal replacement drink, an energy drink, a flavored water, a still water, a carbonated water, a fruit juice, a vegetable juice, a dairy drink, a milk shake, milk, soy milk, or a nut milk (almond milk, cashew milk, hazelnut milk, macadamia milk, peanut milk, or pecan milk). The food product can be a dessert, such as an ice cream, a sorbet, a sherbet, a yogurt, a frozen yogurt, a pudding, a flan, an almond jelly, a Bavarian cream, a pastry cream, a custard and a mousse.

The hyperimmunized egg product can be included in a formulation or composition that can further comprise one or more ingredients suitable for oral administration. In some embodiments, the one or more ingredients comprises a compound that is generally recognized as safe (GRAS) by the FDA. In some embodiments, the GRAS compound is selected from acetic acid, acesulfame potassium, aconitic acid, adipic acid, alginic acid, α-amylase enzyme preparation from *Bacillus stearothermophilus*, aspartame, bromelain, caprylic acid, mixed carbohydrase and protease enzyme product, citric acid, catalase (bovine liver), lactic acid, enzyme-modified lecithin, linoleic acid, malic acid, potassium acid tartrate, propionic acid, stearic acid, succinic acid, tartaric acid, diacetyl tartaric acid esters of mono- and diglycerides, agar-agar, brown algae, red algae, ammonium alginate, ammonium bicarbonate, ammonium carbonate, ammonium chloride, ammonium hydroxide, ammonium citrate dibasic, ammonium phosphate (monobasic), ammonium phosphate (dibasic), ammonium sulfate, bacterially-derived carbohydrase enzyme preparation, bacterially-derived protease enzyme preparation, bentonite, calcium acetate, calcium alginate, calcium carbonate, calcium chloride, calcium citrate, calcium glycerophosphate, calcium hydroxide, calcium iodate, calcium lactate, calcium oxide, calcium pantothenate, calcium propionate, calcium stearate, calcium sulfate, carbon dioxide, beta-carotene, cellulase enzyme preparation derived from *Trichoderma longibrachiatum*, clove and its derivatives, cocoa butter substitute, copper gluconate, copper sulfate, corn silk and corn silk extract, cuprous iodide, L-cysteine, L-cysteine monohydrochloride, dextrin, diacetyl, dill and its derivatives, enzyme-modified fat, ethyl alcohol, ethyl formate, ferric ammonium citrate, ferric chloride, ferric citrate, ferric phosphate, ferric pyrophosphate, ferric sulfate, ferrous ascorbate, ferrous carbonate, ferrous citrate, ferrous fumarate, ferrous gluconate, ferrous lactate, ferrous sulfate, ficin, garlic and its derivatives, glucono delta-lactone, corn gluten, wheat gluten, glyceryl monooleate, glyceryl monostearate, glyceryl behenate, glyceryl palmitostearate, acacia (gum arabic), gum ghatti, guar gum, locust (carob) bean gum, karaya gum (sterculia gum), gum tragacanth, gellan gum, xanthan gum, inositol, insoluble glucose isomerase enzyme preparations, iron, elemental, isopropyl citrate, lactase enzyme preparation from *Candida pseudotropicalis*, lactase enzyme preparation from *Kluyveromyces lactis*, lecithin, licorice and licorice derivatives, ground limestone, animal lipase, lipase enzyme preparation derived from *Rhizopus niveus*, magnesium carbonate, magnesium chloride, magnesium hydroxide, magnesium oxide, magnesium phosphate, magnesium stearate, magnesium sulfate, malt, maltodextrin, malt syrup (malt extract), manganese chloride, manganese citrate, manganese gluconate, manganese sulfate, menhaden oil, methylparaben, microparticulated protein product, monk fruit sweetener, mono- and diglycerides, monosodium phosphate derivatives of mono- and diglycerides, niacin, niacinamide, nisin preparation, nitrogen, nitrous oxide, peptones, rapeseed oil, ox bile extract, pancreatin, papain, pectins, pepsin, potassium alginate, potassium bicarbonate, potassium carbonate, potassium chloride, potassium citrate, potassium hydroxide, potassium iodide, potassium iodate, potassium lactate, potassium sulfate, propyl gallate, propylene glycol, propylparaben, pyridoxine hydrochloride, rennet (animal-derived) and chymosin preparation (fermentation-derived), riboflavin, riboflavin-5-phosphate (sodium), rue, oil of rue, saccharine, selenium, shea nut oil, sodium acetate, sodium alginate, sodium benzoate, sodium bicarbonate, sodium carbonate, sodium citrate, sodium diacetate, sodium hydroxide, sodium hypophosphite, sodium lactate, sodium metasilicate, sodium propionate, sodium sesquicarbonate, sodium tartrate, sodium potassium tartrate, sorbitol, stannous chloride (anhydrous and dihydrated), stearyl citrate, stevia, sucralose, thiamine hydrochloride, thiamine mononitrate, α-tocopherols, trypsin, urea, urease enzyme preparation from *Lactobacillus fermentum*, vitamin A, vitamin B12, vitamin D, beeswax (yellow and white), candelilla wax, carnauba wax, whey, reduced lactose whey, reduced minerals whey, whey protein concentrate, baker's yeast extract, brewer's yeast extract, zein, and aminopeptidase enzyme preparation derived from Lactococcus lactis, or any combination thereof. Other components that can be included in the formulation or composition with the hyperimmunized egg product include albumin, ovalbumin, dextrose, immunostimulants such as inulin, Ashwagandha extract, low calorie or non-nutritive sweeteners such as stevia, sucralose, monk fruit sweetener, aspartame, neotame, and acesulfame potassium, coloring agents, flavoring agents, agents that improve flow properties such as silicon, silicon derivatives, fumed silica, precipitated silica, tricalcium phosphate, powdered cellulose, calcium silicate, magnesium silicate. Any one GRAS compound or a combination thereof, and/or any one other component or combination thereof, can be included in an amount from about 0.0001 wt % to 80 wt % based on the total weight of the formulation or composition.

In order to make the anti-SGLT containing hyperimmunized egg product or isolated anti-SGLT IgY, such as an anti-SGLT1 containing hyperimmunized egg product or isolated anti-SGLT1 IgY, into a user-friendly consumable product, the hyperimmunized egg product or isolated anti-SGLT1 IgY can be formulated into a readily water-soluble powder form. The formulation, in which the IgY activity was unaffected, can be a blend of maltodextrin (10-60 wt %), hyperimmunized egg product or isolated anti-SGLT1 IgY (0.001-10 wt %), dextrose (10-30 wt %), Aerosil® fumed silica (1-10 wt %), flavoring agent (1-10 wt %), stevia or any other sweetener (0.1-10 wt %), and a coloring agent (0.0001-0.001 wt %), can be blended together into a powder and packaged into a sachet, which can be added to a fluid, such as water or a juice, to prepare a beverage for consuming. Another exemplary formulation includes hyperimmunized egg product or isolated anti-SGLT1 IgY (0.001-10 wt %), Ashwagandha extract (1-10 wt %), inulin (10-40 wt %), citric acid (0.1-10 wt %), sodium benzoate (0.1-10 wt %), flavoring agent (0.1-10 wt %), a sweetener such as, but not limited to sucralose, stevia, monk fruit sweetener, aspartame, neotame, or acesulfame potassium (0.001-0.05 wt %), and a coloring agent (0.0001-0.001 wt %). Unsweetened formulations that do not include a sweetener also can be provided, such as for adding to a fruit juice to provide the final beverage composition.

In certain embodiments, the composition comprises one or more additional compounds, e.g., a nutrient or probiotic. For example, in one embodiment, the composition is integrated into a dietary supplement. One method for preparing the egg to be incorporated into a dietary supplement involves drying the egg into an egg powder. Although various methods are known for drying eggs, spray drying is a preferred method. The process of spray drying eggs is well known in the art. For example, spray drying can be achieved by spraying the whole egg liquid or egg yolk liquid for 1 to 5 seconds at an inlet temperature 160° C. to 190° C. in a drying the chamber at a temperature of 60° C. to 90° C. In some embodiments, the composition is an aqueous solution comprising the nanoparticle or microparticle. In some embodiments, the hyperimmunized egg product for encapsulation is a liquid or a freeze-dried powder.

In certain embodiments, whole eggs are divided into separate fractions such as egg yolks and egg whites. For example, it is generally known in the art that IgY antibody is found in egg yolks. Accordingly, those having ordinary skill in the art would clearly recognize that separation of egg yolks could provide more potent fractions or elimination of undesirable components. Such further separation can provide for the ability to make encapsulated products and compositions comprising the egg or fraction thereof.

The composition can be administered to the subject in an amount that is effective in lowering blood glucose for treating or preventing a particular disorder. Dosage and duration of the administration will depend upon the particular condition of the subject. In some embodiments, the composition can be administered to the subject for at least 5, 6, 7, 8, 9, 10, 11, 12, 13, 14, 15, 20, 25, 30, 60, 90, 180 or 365 days. The composition can be administered to the subject 1, 2, 3, 4, 5, 6, or more times per day. Any of these values may be used to define a range for the number of times the composition may be administered to the subject per day. For example, in some embodiments the composition is administered to the subject 1-2 times per day, 1-3 times per day, or 1-4 times per day. In some embodiments, the composition is administered to the subject at least twice per day. In some embodiments, the composition is administered to subject at least once per day. In some embodiments, the composition is administered to the subject daily. In some embodiments, the composition is administered to the subject once every two days. In some embodiments, the composition is administered to the subject once every three days. In some embodiments, the composition is administered to the subject once per week. In some embodiments, composition is administered to the subject once per day for more than 10 consecutive days.

In some embodiments, the composition administered to the subject comprises a hyperimmunized egg or hyperimmunized egg product. In some embodiments, daily amounts ranging from less than one to several whole, hyperimmune eggs (or hyperimmune egg products containing the equivalent of less than one to several whole, hyperimmune eggs) can be administered to the subject depending on the particular circumstance of the condition. More potent fractions can be separated and concentrated by methods well-known in the art, from several hundred eggs.

In some embodiments, daily amounts ranging from less than one to several whole, hyperimmune eggs (or hyperimmune egg products containing the equivalent of less than one to several whole, hyperimmune eggs) can be administered to the subject depending on the particular circumstance of the condition. More potent fractions can be separated and concentrated by methods well-known in the art, from several hundred eggs.

In certain embodiments, the effective amount of the hyperimmunized egg product administered to a subject (e.g., a human) is 0.1, 0.2, 0.3, 0.4, 0.5, 0.6, 0.7, 0.8, 0.9, 1, 2, 3, 4, 5, 6, 7, 8, 9, 10, 20, 30, 40 or 50 grams per day. For example, in some embodiments, 0.1, 0.2, 0.3, 0.4, 0.5, 0.6, 0.7, 0.8, 0.9, 1, 2, 3, 4, 5, 6, 7, 8, 9, 10, 20, 30, 40 or 50 grams per day of whole egg are administered to the subject. In some embodiments, 0.1, 0.2, 0.3, 0.4, 0.5, 0.6, 0.7, 0.8, 0.9, 1, 2, 3, 4, 5, 6, 7, 8, 9, 10, 20, 30, 40 or 50 grams per day of egg yolk are administered to the subject. In some embodiments, 0.1, 0.2, 0.3, 0.4, 0.5, 0.6, 0.7, 0.8, 0.9, 1, 2, 3, 4, 5, 6, 7, 8, 9 or 10 grams per day of dried egg yolk or dried whole egg are administered to the subject. Any of these values may be used to define a range for the effective amount of the hyperimmunized egg product administered to the mammal. For example, in some embodiments the effect amount of the hyperimmunized egg product is between 0.1 and 10 grams, between 0.5 to 6 grams, or between 1 and 5 grams per day. In a particular embodiment, 3 grams of egg yolk are administered to the subject (e.g., a human) per day.

In certain embodiments, the composition comprises at least 0.01%, 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98% or 99% w/w of the hyperimmunized egg product. Any of these values may be used to define a range for the concentration of the hyperimmunized egg product in the composition. For example, in some embodiments, the composition comprises between 0.01% and 50%, between 0.1% and 50%, or between 1% and 50% w/w of the hyperimmunized egg product.

In some embodiments, the hyperimmunized egg product is administered as a beverage, e.g., a beverage comprising one or more flavoring agents, coloring agents and/or artificial sweeteners. In certain embodiments, the hyperimmunized egg product is administered as a composition comprising one or more additional compounds, e.g., a nutrient or probiotic. For example, in one embodiment, the hyperimmunized egg product of the invention is integrated into a dietary supplement. One method for preparing the egg of the invention to be incorporated into a dietary supplement involves drying the egg into an egg powder. Although various methods are known for drying eggs, spray drying is a preferred method. The process of spray drying eggs is well known in the art.

In other embodiments, the hyperimmunized egg product can be processed to produce a purified or partially purified IgY. The purified or partially purified IgY can be administered by intravenous injection. Any of several known pharmaceutically acceptable carriers can be used in the preparation of an injectable or otherwise administrable preparation, including phosphate buffered saline, saline, and water for injection. The purified or partially purified IgY can be administered by injection, for example, intravenous, subcutaneous, or intramuscular injection.

Methods of purifying and concentrating IgY antibodies from egg products are known in the art and are described, for example, in U.S. Pat. No. 5,367,054 (Lee, (1994)), which is incorporated by reference herein in its entirety. The IgY antibody can be purified or partially purified using polyethylene glycol (PEG) precipitation. The IgY antibody can be purified or partially purified by separation of water soluble antibodies into an aqueous layer at different pH by freeze thaw methods followed by NaCl precipitation. The IgY antibody can be purified or partially purified by separation using affinity chromatography.

EXAMPLES

The following examples are included for illustrative purposes only and are not intended to limit the scope of the embodiments provided herein.

1. Generation of Anti-SGLT1 Peptide Chicken IgY and Efficacy in a Human Intestinal Cell Line Model of Glucose Uptake Chicken IgY antibodies were generated using the 19 amino acid human SGLT1 peptide antigen shown in FIG. 1 (SEQ ID NO:1) and tested for binding specificity to the peptide using an ELISA assay. The SGLT1 peptide was injected into chickens at least three times to boost the titer of IgY harvested from the eggs. FIG. 2 shows the binding of three IgY preparations to the antigen peptide coated on the plate. In FIG. 2—the first batch of IgY after immunization is labeled "old" in figure, the second batch of IgY after immunization harvested after few days later is labeled "new" in the figure, and finally a non-specific IgY (anti-snake venom IgY, labeled "snake IgY" in the figure), was used to demonstrate binding. As can be seen in FIG. 2, there was very high binding of first batch IgY against SGLT1 peptide antigen (absorbance OD>2) suggesting high titer of anti-SGLT peptide IgY was elicited. The second batch was less effective in binding and the third IgY (nonspecific IgY) showed very low binding. The IgY antibodies from the first batch were chosen for all future studies.

2. Glucose Uptake Inhibition Studies

Figure 3:
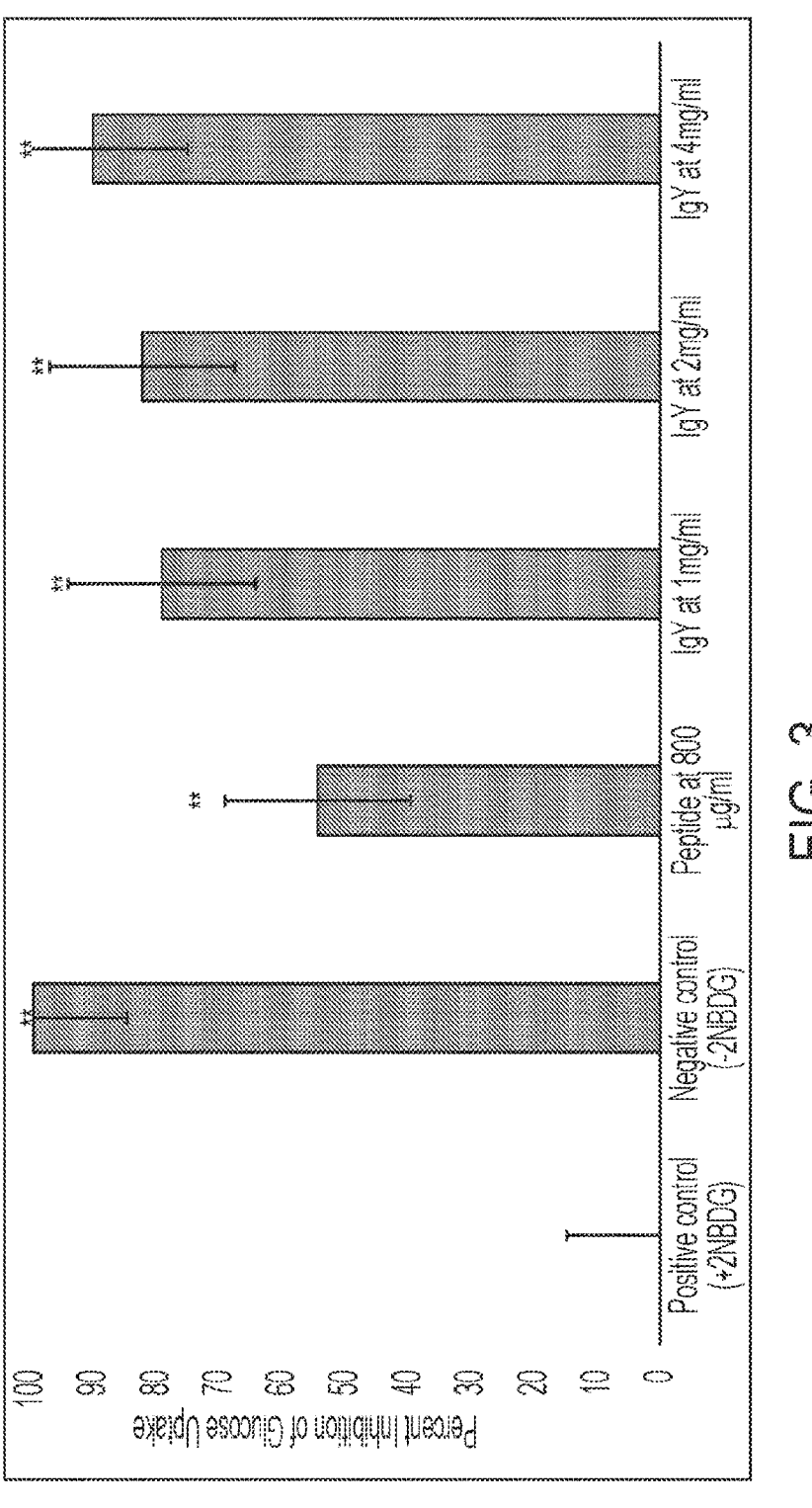
FIG. 3 is a graph showing percent inhibition of glucose uptake by different concentrations of IgY antibodies to SGLT peptide antigen.

The IgY antibodies were then tested for their ability to inhibit the uptake of glucose in a human intestinal cell line CaCo2, which expresses SGLT1. The results of the inhibition studies are shown in FIG. 3. The data in FIG. 3 are shown as percent inhibition of glucose uptake relative to glucose uptake in the absence of any intervention. As can be seen in FIG. 3, the peptide used as antigen (800 μg/ml) was able to block the uptake of glucose, likely because it interferes with the glucose binding to cell surface SGLT1. The anti-SGLT1 IgY was able to almost completely block glucose uptake at the highest concentration tested with lower concentrations also showing good inhibition. These data show that the anti SGLT1 IgY is active and can inhibit glucose uptake. In the figure, ** is P<0.01 Student's t-tests were performed to compare between the glucose inhibition shown by controls, peptide, and different concentration of IgY antibodies.

3. Animal Study Demonstrating Efficacy of Anti-SGLT1 IgY

An animal study was conducted to assess the effect of administering the anti-SGLT1 IgY antibody in an Oral Glucose Tolerance Test (OGTT) model in Wistar rats. The OGTT test was performed to determine if an intervention has blocked the intestinal absorption of orally given glucose load, and then lowering of the increase in blood glucose levels is observed.

The animals were acclimatized and were randomly distributed into 6 groups, each group comprised of 6 rats. The rats in group G1 served as a normal control group and were administered the vehicle (normal saline) alone at the dose volume of 10 mL/kg, whereas the rats in groups G2 and G3 were administered metformin and anti-SGLT1 IgY antibody, respectively, at the doses of 200 mg/kg and 500 mg/kg body weight for single administration.

All the rats were observed for clinical signs, morbidity, and mortality, and body weight and blood glucose were measured during the study period.

The animals were assigned into 3 different treatment groups as shown below

TABLE 1

Treatment Groups.

| Group No. | Group Description | Dose | No. of Rats | Animal Accession No. From | To |
|---|---|---|---|---|---|
| G1 | Normal Control | 0 mg/kg | 6 | Ra3911 | Ra3916 |
| G2 | Metformin | 200 mg/kg | 6 | Ra3917 | Ra3922 |
| G3 | Anti-SGLT1 IgY | 500 mg/kg | 6 | Ra3923 | Ra3928 |

Test Procedure

Single administration of vehicle (normal saline) and test item (metformin or anti-SGLT1 IgY antibody were administered for respective groups. After 30 minutes, glucose was administered at a dose of 2 gm/kg to each group to initiate an Oral Glucose Tolerance Test (OGTT). The OGTT studies were conducted on overnight fasting animals. Average fasting glucose values were 100-120 mg/dl. 0 minute (before glucose administration), after glucose administration 30 minutes, 60 minutes, 90 minutes, 120 minutes, and 180 minutes glucose level values were measured by using an Accu-Chek® glucometer (Roche Diabetes Care, Inc., Indianapolis, IN). The data is shown in Tables 2 through 7.

TABLE 2

Summary of clinical signs and mortality. (Single dose OGTT study)

| Group No. | Sex | Treatment | Dose (mg/kg) | Total Number of animals | Clinical Signs | Mortality |
|---|---|---|---|---|---|---|
| G1 | M | Normal Control | 0 mg/kg | 6 | 1//6 | 0/6 |
| G2 | M | METFORMIN | 200 mg/kg | 6 | 1/6 | 0/6 |
| G3 | M | ANTI-SGLT1 IGY | 500 mg/kg | 6 | 1/6 | 0/6 |

Key:
M: Male;
'0' mortality of '6' animals observed;
'1' indicates normal;
(6) indicates number of animals observed

TABLE 3

Summary of Body Weights (g). (Single Dose OGTT Study)

| Groups | | Day −01 Males |
|---|---|---|
| G1 | Mean | 228.02 |
| | ±SD | 10.27 |
| | N | 6 |
| G2 | Mean | 232.63 |
| | ±SD | 9.17 |
| | N | 6 |

TABLE 3-continued

Summary of Body Weights (g). (Single Dose OGTT Study)

| Groups | | Day −01 Males |
|---|---|---|
| G3 | Mean | 231.18 |
| | ±SD | 9.41 |
| | N | 6 |

TABLE 4

Individual Animal Clinical Signs Observations. (Single dose OGTT study)

| Group | Animal No. | Sex | Day 01 |
|---|---|---|---|
| G1 | Ra3911 | Male | 1 |
| | Ra3912 | | 1 |
| | Ra3913 | | 1 |
| | Ra3914 | | 1 |
| | Ra3915 | | 1 |
| | Ra3916 | | 1 |
| G2 | Ra3917 | | 1 |
| | Ra3918 | | 1 |
| | Ra3919 | | 1 |
| | Ra3920 | | 1 |
| | Ra3921 | | 1 |
| | Ra3922 | | 1 |
| G3 | Ra3923 | | 1 |
| | Ra3924 | | 1 |
| | Ra3925 | | 1 |
| | Ra3926 | | 1 |
| | Ra3927 | | 1 |
| | Ra3928 | | 1 |

Key: 1—Normal.

TABLE 5

Individual Animal body weight (g). (Single dose OGTT study)

| Group | Animal No. | Sex | Day 01 |
|---|---|---|---|
| G1 | Ra3911 | Male | 213.00 |
| | Ra3912 | | 235.47 |
| | Ra3913 | | 238.74 |
| | Ra3914 | | 218.37 |
| | Ra3915 | | 228.35 |
| | Ra3916 | | 234.21 |

TABLE 5-continued

| Individual Animal body weight (g). (Single dose OGTT study) | | | |
|---|---|---|---|
| Group | Animal No. | Sex | Day 01 |
| G2 | Ra3917 | | 239.55 |
| | Ra3918 | | 215.70 |
| | Ra3919 | | 237.58 |
| | Ra3920 | | 239.11 |
| | Ra3921 | | 234.99 |
| | Ra3922 | | 228.86 |

TABLE 5-continued

| Individual Animal body weight (g). (Single dose OGTT study) | | | |
|---|---|---|---|
| Group | Animal No. | Sex | Day 01 |
| G3 | Ra3923 | | 226.72 |
| | Ra3924 | | 240.05 |
| | Ra3925 | | 214.78 |
| | Ra3926 | | 231.00 |
| | Ra3927 | | 238.15 |
| | Ra3928 | | 236.35 |

TABLE 6

Summary of blood glucose level values (mg/dL) (Single dose OGTT study)

| Groups | Sex | | Time in Minutes | | | | | |
|---|---|---|---|---|---|---|---|---|
| | | | 0 | 30 | 60 | 90 | 120 | 180 |
| G1 | Male | Mean | 105.67 | 187.00 | 146.00 | 136.33 | 127.83 | 110.17 |
| (Normal | | SD | 5.09 | 7.85 | 8.53 | 6.41 | 4.12 | 3.13 |
| control) | | | | | | | | |
| G2 | | Mean | 108.17 | 161.67** | 127.17* | 121.50* | 114.00** | 106.33** |
| (Metformin) | | SD | 3.87 | 3.39 | 2.79 | 4.89 | 5.93 | 3.50 |
| G3 | | Mean | 104.50 | 164.17** | 128.17** | 125.83** | 115.67** | 107.50 |
| (Anti SGLT1-IgY) | | SD | 4.51 | 12.04 | 8.13 | 5.60 | 4.59 | 3.21 |

Note:

The values are expressed in Mean ± SD: (n = 6) *P < 0.01, P < 0.001, *P < 0.0001 as compared to induction control (G1) group.

Figure 4:
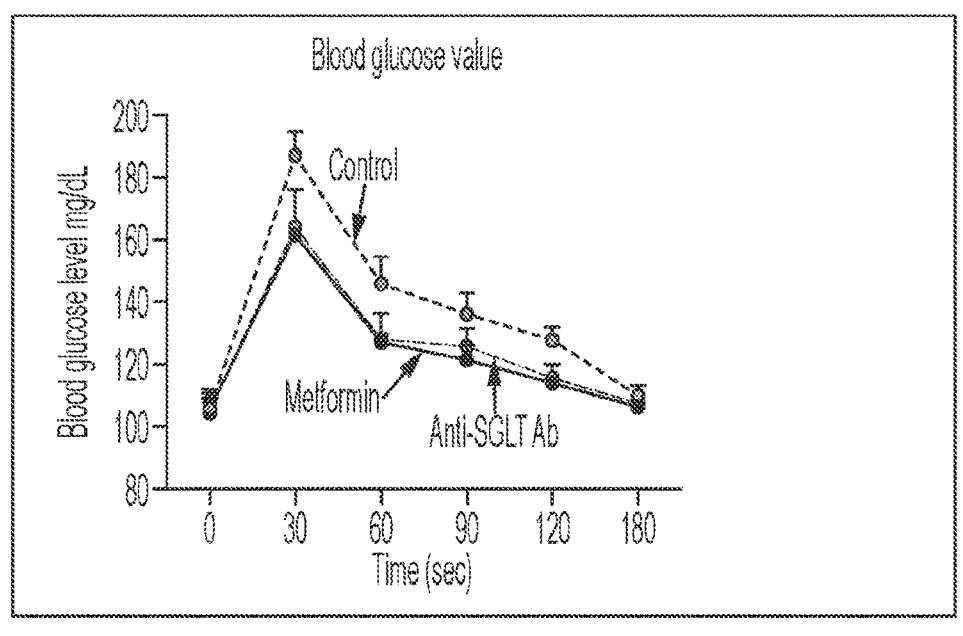
FIG. 4 is a graph showing blood glucose levels after administering the IgY antibodies to SGLT peptide antigen compared to administration of metformin.

FIG. 4 shows a graphical representation of blood glucose levels from Table 6. As can be seen in FIG. 4, the administration of the anti-SGLT1-IgY antibody appeared to be as effective as metformin in reducing glucose uptake.

TABLE 7

Summary of area under curve values (mg/dL) (Single dose OGTT study)

| Groups | Sex | | Time in Minutes | | | | | |
|---|---|---|---|---|---|---|---|---|
| | | | 0 | 30 | 60 | 90 | 120 | 180 |
| G1 | Male | Mean | 0.00 | 9.76 | 11.10 | 9.41 | 8.81 | 3.97 |
| (Normal | | SD | 0.00 | 0.34 | 0.52 | 0.47 | 0.33 | 0.10 |
| control) | | | | | | | | |
| G2 | | Mean | 0.00 | 8.99* | 9.63** | 8.29** | 7.85** | 3.67** |
| (Metformin) | | SD | 0.00 | 0.19 | 0.20 | 0.20 | 0.35 | 0.14 |
| G3 | | Mean | 0.00 | 8.96** | 9.74*** | 8.47** | 8.07** | 3.72** |
| (Anti SGLT1-IgY) | | SD | 0.00 | 0.28 | 0.65 | 0.42 | 0.33 | 0.09 |

Note:

The values are expressed in Mean ± SD: (n = 6) *P < 0.01, P < 0.001, *P < 0.0001 as compared to induction control (G1) group.

Figure 5:
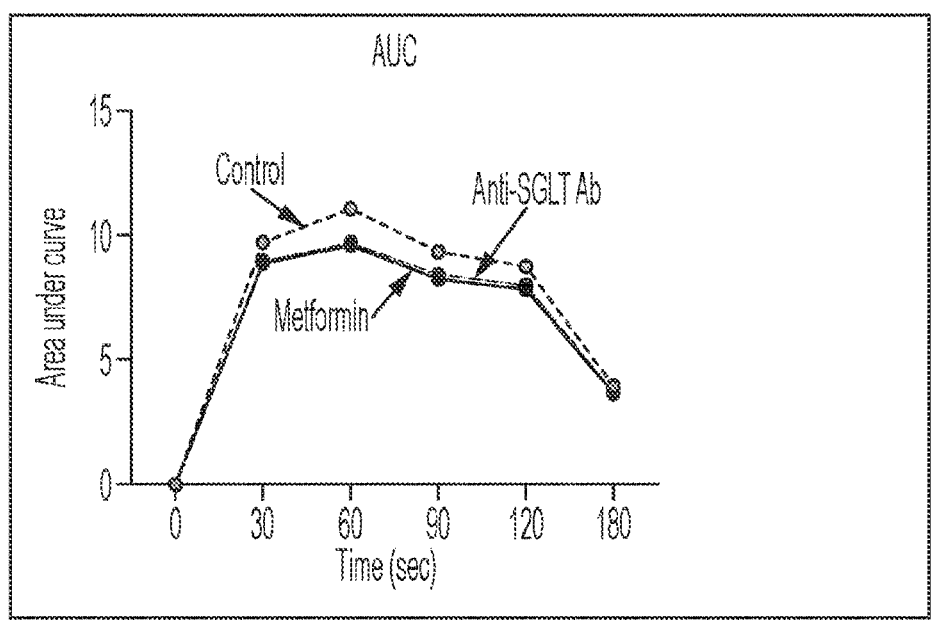
FIG. 5 is a graph showing area under the curve (AUC) comparing administration of the IgY antibodies to SGLT peptide antigen provided herein to administration of metformin.

FIG. 5 shows a graphical representation of AUC values from Table 7. As can be seen in FIG. 5, the administration of the anti-SGLT1-IgY antibody appeared to be as effective as metformin.

Salient Experimental Findings are Presented Below:

1. In-life parameters: No clinical signs or morbidity were observed in any of the treatment groups. The body weights were unaffected by the treatment groups.

2. Single dose OGTT Study: Significantly decreased the blood glucose level of G2 and G3 groups (30, 60, 90 and 120 min) when compared to normal control group G1 after 2 g/kg oral administration of glucose.

3. Significantly decreased the area under curve of G2 and G3 groups (30, 60, 90 and 120 min) when compared to normal control group G1 after 2 g/kg oral administration of glucose.

There were no significant difference observed between the G2 and G3.

From the results, in can be concluded that a single dose administration of anti-SGLT-1 IgY antibody (G3) at 500 mg/kg results in highly statistically significant decreased glucose absorption and distribution in blood after oral administration of 2 g/kg glucose.

4. Proposed Clinical Trial Design for Anti-SGLT1 IgY

A clinical trial for testing anti-SGLT1 IgY antibodies for their ability to reduce glucose uptake is planned. The trial design is to include prediabetic or diabetic patients (n=100). Oral dosing of the anti-SGLT1 IgY antibodies to subjects in a fasting state, followed by Oral Glucose Tolerance Testing, with end points of 1, 15, 30, 60 and 120 minutes post glucose-ingestion, for blood glucose measurements.

References

Sodium glucose cotransporter SGLT1 as a therapeutic target in diabetes mellitus

P Song et al., Expert opinion on Therapeutic Targets 20(9): 1109-1125 (2016).

Na⁺-d-glucose Cotransporter SGLT1 is Pivotal for Intestinal Glucose Absorption and Glucose-Dependent Incretin Secretion V Gorboulev et al., Diabetes 61(1): 187-196 (2012).

SGLT1 inhibition: Pros and cons

V Tsimihodimos et al., European journal of Physiology 838:153-156 (2018).

Intestinal SGLT1 in metabolic health and disease

A Lehmann et al., Am J Physiol Gastrointest Liver Physiology 310(11): G887-G898 (2016)

SGLT1 is a novel cardiac glucose transporter that is perturbed in disease states SK Banerjee et al., Cardiovasc Res 84(1): 111-118 (2009).

Defects in Na+/glucose cotransporter (SGLT1) trafficking and function cause glucose-galactose malabsorption MG Martin et al., Nature Genetics 12(2): 216-220 (1996).

Structure of the human Na+/glucose cotransporter gene SGLT1.

E Turk et ali., Journal of Biological Chemistry 269(21): 15204-15209 (1994).

Improved glycemic control in mice lacking Sglt1 and Sglt2

DR Powell et al., Am J Physiol Endocrinol Metab 304(2): E117-130(2013).

I claim:

1. An antibody characterized in that it binds to an extracellular glucose binding domain of a sodium—glucose co-transporter SGLT comprising a sequence selected from among:

```
                                        (SEQ ID NO: 1)
QSGQLFDYIQSITSYLGPP, (SEQ ID NO: 2)
QGGQLFDYIQAVSSYLAPP, (SEQ ID NO: 3)
QGGQLFDYIQSVSSYLAPP, (SEQ ID NO: 4)
QNGQLIHYIESISSYLGPP, (SEQ ID NO: 5)
QNGQLFHYIGSVSSYLGPP, (SEQ ID NO: 6)
QGGQLVHYIEAISSYLGPP, (SEQ ID NO: 7)
QGGQLIHYIEAISSYLGPP,
and (SEQ ID NO: 8)
QNGQLFHYISSFSSYIGPP.
```

2. A pharmaceutical composition, comprising:
the antibody of claim 1; and
a pharmaceutically acceptable carrier.

3. The pharmaceutical composition of claim 2 formulated for oral administration.

4. A hyperimmunized egg produced by an avian that has been hyperimmunized with an antigen that comprises an extracellular glucose binding domain of a sodium—glucose co-transporter SGLT, wherein a level of antibodies to the antigen in the hyperimmunized egg is increased relative to an egg from an animal that has not been hyperimmunized, wherein the antigen comprises a sequence selected from among:

```
                                        (SEQ ID NO: 1)
QSGQLFDYIQSITSYLGPP, (SEQ ID NO: 2)
QGGQLFDYIQAVSSYLAPP, (SEQ ID NO: 3)
QGGQLFDYIQSVSSYLAPP, (SEQ ID NO: 4)
QNGQLIHYIESISSYLGPP, (SEQ ID NO: 5)
QNGQLFHYIGSVSSYLGPP, (SEQ ID NO: 6)
QGGQLVHYIEAISSYLGPP, (SEQ ID NO: 7)
QGGQLIHYIEAISSYLGPP,
and (SEQ ID NO: 8)
QNGQLFHYISSFSSYIGPP.
```

5. A hyperimmunized egg product obtained from the hyperimmunized egg of claim 4.

6. The hyperimmunized egg product of claim 5, wherein:

a) the hyperimmunized egg product is whole egg, egg yolk, or purified or partially purified polyclonal IgY antibody to the extracellular glucose binding domain of a sodium—glucose co-transporter SGLT; or b) the hyperimmunized egg product is a liquid, a spray-dried powder, or a freeze-dried powder.

7. A pharmaceutical composition, comprising:

the hyperimmunized egg product of claim 5; and a pharmaceutically acceptable carrier, wherein the pharmaceutical composition is formulated for oral administration.

8. A formulation, comprising:

a) an isolated polyclonal IgY antibody characterized in that it binds to an extracellular glucose binding domain of a sodium—glucose co-transporter SGLT comprising a sequence selected from the group consisting of:

```
                              (SEQ ID NO: 1)
QSGQLFDYIQSITSYLGPP, (SEQ ID NO: 2)
QGGQLFDYIQAVSSYLAPP, (SEQ ID NO: 3)
QGGQLFDYIQSVSSYLAPP, (SEQ ID NO: 4)
QNGQLIHYIESISSYLGPP, (SEQ ID NO: 5)
QNGQLFHYIGSVSSYLGPP, (SEQ ID NO: 6)
QGGQLVHYIEAISSYLGPP, (SEQ ID NO: 7)
QGGQLIHYIEAISSYLGPP,
and (SEQ ID NO: 8)
QNGQLFHYISSFSSYIGPP;
``` or b) a hyperimmunized egg product obtained from a hyperimmunized egg produced by an avian that has been hyperimmunized with an antigen that comprises an extracellular glucose binding domain of a sodium—glucose co-transporter SGLT, wherein a level of antibodies to the antigen in the hyperimmunized egg is increased relative to an egg from an animal that has not been hyperimmunized, wherein the antigen comprises a sequence selected from among:

```
                              (SEQ ID NO: 1)
QSGQLFDYIQSITSYLGPP, (SEQ ID NO: 2)
QGGQLFDYIQAVSSYLAPP, (SEQ ID NO: 3)
QGGQLFDYIQSVSSYLAPP, (SEQ ID NO: 4)
QNGQLIHYIESISSYLGPP, (SEQ ID NO: 5)
QNGQLFHYIGSVSSYLGPP, (SEQ ID NO: 6)
QGGQLVHYIEAISSYLGPP, (SEQ ID NO: 7)
QGGQLIHYIEAISSYLGPP,
and (SEQ ID NO: 8)
QNGQLFHYISSFSSYIGPP;
``` and one or more than one GRAS component.

9. The formulation as claimed in claim 8, wherein;

a) the formulation is in a form selected from the group consisting of nanoparticles, a nano-emulsion, an emulsion, a powder, a tablet, an enterically coated tablet, a capsule, an enterically coated capsule, a suspension, a solution, and an oral beverage; or b) the formulation is prepared using a whole hyperimmune egg containing the antibody, a hyperimmune egg yolk containing the antibody, a spray-dried whole egg powder containing the antibody, a spray-dried egg yolk powder containing the antibody, a freeze-dried whole egg powder containing the antibody, a freeze-dried egg yolk powder containing the antibody, or a purified polyclonal IgY antibody.

\* \* \* \* \*

```
                         SEQUENCE LISTING

Sequence total quantity: 8
SEQ ID NO: 1            moltype = AA   length = 19
FEATURE                 Location/Qualifiers
source                  1..19
                        mol_type = protein
                        note = extracellular glucose binding domain of a sodium
                         glucose cotransporter SGLT1
                        organism = synthetic construct
SEQUENCE: 1
QSGQLFDYIQ SITSYLGPP                                                  19

SEQ ID NO: 2            moltype = AA   length = 19
FEATURE                 Location/Qualifiers
source                  1..19
                        mol_type = protein
                        note = extracellular glucose binding domain of a sodium
                         glucose cotransporter SGLT2
                        organism = synthetic construct
SEQUENCE: 2
QGGQLFDYIQ AVSSYLAPP                                                  19

SEQ ID NO: 3            moltype = AA   length = 19
FEATURE                 Location/Qualifiers
source                  1..19
                        mol_type = protein
                        note = extracellular glucose binding domain of a sodium
                         glucose cotransporter SGLT2
                        organism = synthetic construct
SEQUENCE: 3
QGGQLFDYIQ SVSSYLAPP                                                  19

SEQ ID NO: 4            moltype = AA   length = 19
FEATURE                 Location/Qualifiers
source                  1..19
                        mol_type = protein
                        note = extracellular glucose binding domain of a sodium
                         glucose cotransporter SGLT3
                        organism = synthetic construct
SEQUENCE: 4
QNGQLIHYIE SISSYLGPP                                                  19
```

-continued

```
SEQ ID NO: 5           moltype = AA   length = 19
FEATURE                Location/Qualifiers
source                 1..19
                       mol_type = protein
                       note = extracellular glucose binding domain of a sodium
                        glucose cotransporter SGLT3b
                       organism = synthetic construct
SEQUENCE: 5
QNGQLFHYIG SVSSYLGPP                                            19

SEQ ID NO: 6           moltype = AA   length = 19
FEATURE                Location/Qualifiers
source                 1..19
                       mol_type = protein
                       note = extracellular glucose binding domain of a sodium
                        glucose cotransporter SGLT3a
                       organism = synthetic construct
SEQUENCE: 6
QGGQLVHYIE AISSYLGPP                                            19

SEQ ID NO: 7           moltype = AA   length = 19
FEATURE                Location/Qualifiers
source                 1..19
                       mol_type = protein
                       note = extracellular glucose binding domain of a sodium
                        glucose cotransporter SGLT3a
                       organism = synthetic construct
SEQUENCE: 7
QGGQLIHYIE AISSYLGPP                                            19

SEQ ID NO: 8           moltype = AA   length = 19
FEATURE                Location/Qualifiers
source                 1..19
                       mol_type = protein
                       note = extracellular glucose binding domain of a sodium
                        glucose cotransporter SGLT3b
                       organism = synthetic construct
SEQUENCE: 8
QNGQLFHYIS SFSSYIGPP                                            19
```